United States Patent [19]

Kato et al.

[11] Patent Number: 4,943,655
[45] Date of Patent: Jul. 24, 1990

[54] SALT OF 5-ACETYL-2-ALKYLBENZENESULFONIC ACID

[75] Inventors: Kunioki Kato; Masao Kawamura, both of Akashi; Hiroshi Goda, Himeji; Kiyoshi Sawada, Hyogo; Kazuhiro Hamatani, Kakogawa, all of Japan

[73] Assignee: Seitetsu Kagaku Co., Ltd., Japan

[21] Appl. No.: 328,388

[22] Filed: Mar. 24, 1989

Related U.S. Application Data

[60] Division of Ser. No. 178,833, Mar. 25, 1988, Pat. No. 4,853,158, which is a continuation of Ser. No. 20,242, Mar. 2, 1987, abandoned, which is a continuation of Ser. No. 733,832, May 14, 1985, abandoned.

[30] Foreign Application Priority Data

May 15, 1984 [JP] Japan .................. 59-98327
May 15, 1984 [JP] Japan .................. 59-98328
Sep. 18, 1984 [JP] Japan .................. 59-196470
Apr. 3, 1985 [JP] Japan .................. 60-71624

[51] Int. Cl.$^5$ .............. C07C 143/28; C07C 143/38; C07C 143.78
[52] U.S. Cl. .................. 562/46; 564/88
[58] Field of Search .................. 562/46

[56] References Cited

FOREIGN PATENT DOCUMENTS 206550 12/1983 Japan ........................ 562/46

Primary Examiner—J. E. Evans
Attorney, Agent, or Firm—Pollock, Vande Sande & Priddy

[57] ABSTRACT

Process for preparing 2-alkyl-5-haloacetylbenzenesulfonamide represented by the general formula (1),

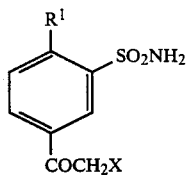
(1)

(wherein $R^1$ is an alkyl group having 1 to 5 carbon atoms; and X is a chlorine atom, bromine atom or iodine atom), characterized by halogenating a 5-acetyl-2-alkylbenzenesulfonamide represented by the general formula (2),

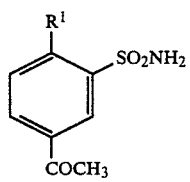
(2)

(wherein $R^1$ is the same as defined above) in a lower alcohol represented by the general formula (3),

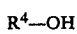

(wherein $R^4$ is an alkyl group having 1 to 5 carbon atoms).

2 Claims, No Drawings

SALT OF 5-ACETYL-2-ALKYLBENZENESULFONIC ACID

This is a divisional of Ser. No. 178,833, filed on Mar. 25, 1988, now U.S. Pat. No. 4,853,158, which in turn is a continuation of 07/020,242 filed on Mar. 2, 1987, now abandoned, which in turn is a continuation of 06/733,832 filed on May 14, 1985, now abandoned.

FIELD OF THE INVENTION

The present invention relates to a process for preparing 2-alkyl-5-haloacetylbenzenesulfonamide.

The 2-alkyl-5-haloacetylbenzenesulfonamide represented by the general formula (1),

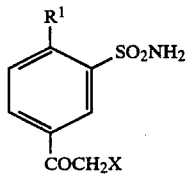

(1)

(wherein $R^1$ is an alkyl group having 1 to 5 carbon atoms; and X is a chlorine atom, bromine atom or iodine atom) which is useful intermediate compound for preparing various pharmaceutical chemicals and agricultural chemicals. For example, 5-bromoacetyl-2-methylbenzenesulfonamide is the intermediate for preparing phenylethanolamine derivatives which are known as hypotensives.

DESCRIPTION OF THE PRIOR ART AND PROBLEMS INVOLVED

There have been known various methods for preparing 5-acetyl-2-alkylbenzenesulfonamide, for example, "Indian Journal of Chemistry, Vol. 18B, 277–279 (1979)" teaches a process for preparing 5-acetyl-2-methylbenzenesulfonamide, by first reacting 4-methylacetophenone with chlorosulfonic acid in chloroform to prepare 5-acetyl-2-methylbenzenesulfonyl chloride, then this product is reacted with ammonia to obtain the desired 5-acetyl-2-methylbenzenesulfonamide as shown in the following reaction scheme.

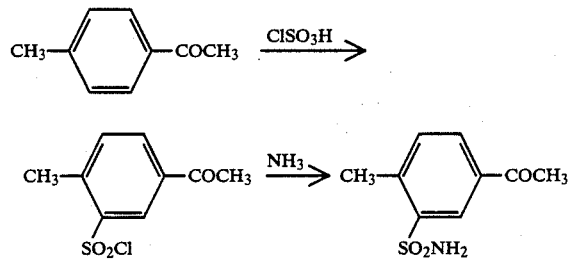

Furthermore, DT-OS 2,843,016 (1979) teaches a process for preparing 5-acetyl-2-methylbenzenesulfonamide, by first diazotizing 3-amino-4-methylacetophenone at a lower temperature, then this diazotized product is reacted with sulfur dioxide gas in the presence of cupric chloride in glacial acetic acid to obtain 5-acetyl-2-methylbenzenesulfonyl chloride, finally this product is reacted with ammonia to obtain 5-acetyl-2-methylbenzenesulfonamide as shown in the following reaction scheme.

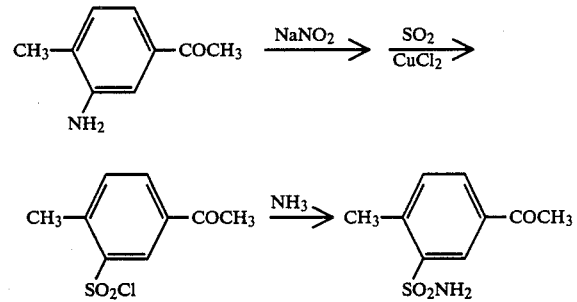

Additionally, as to another process for preparing 2-alkyl-5-haloacetylbenzenesulfonamide, there have been known halogenating method of 5-acetyl-2-alkylbenzenesulfonamide in acetic acid, for example, an invention disclosed in U.K. Patent No. 2,006,772.

However, the above-mentioned method disclosed in "Indian Journal of Chemistry, Vol. 18B, 277–279 (1979)" only teaches that the yield of the desired 5-acetyl-2-methylbenzenesulfonamide is as low as only 30%. Further, the process as disclosed in DT-OS 2,843,016 (1979) is not considered to be an advantageous process from industrial standpoint, since the starting material to be used in this method is expensive, and the diazotization is carried out in lower concentration with lower volume efficiency, as well as it takes a number of process steps. Additionally, the above-mentioned U.K. Patent No. 2,006,772, is also considered not to be an advantageous process from industrial standpoint, for the reason that (1) higher reaction temperature, (2) the yield of the desired product is relatively low, together with the formation of 2-alkyl-5-dihaloacetylbenzenesulfonamide as the by-product, and (3) purification of the desired product by separating the by-product is also difficult.

The present inventors have made extensive studies for overcoming the above-mentioned problems involved in the prior art techniques and finally succeeded in the present invention.

SUMMARY OF THE INVENTION

An object of the present invention is to provide a process for preparing 5-acetyl-2-alkylbenzenesulfonamide through 5-acetyl-2-alkylbenzenesulfonyl chloride by using 4-alkylacetophenone as the starting material which is readily available in the chemical market.

Another object of the present invention is provide a process for halogenating 5-acetyl-2-alkylbenzenesulfonamide by using a lower alcohol which is a relatively inexpensive material readily available in the chemical market.

Further object of the present invention is to provide a process for preparing 2-alkyl-5-haloacetylbenzenesulfonamide.

DETAILED EXPLANATION OF THE INVENTION

The present invention relates to an industrially advantageous process for preparing 2-alkyl-5-haloacetylbenzenesulfonamide. Thus according to the present invention, 4-alkylacetophenone is sulfonated with sulfuric anhydride or fuming sulfuric acid in concentrated sulfuric acid, the resulting 5-acetyl-2-alkylbenzenesulfonic acid or its salt is reacted with an N,N-dialkylaniline or its protonic acid salt to obtain N,N-dialkylaniline salt of 5-acetyl-2-alkylbenzenesulfonic acid, then the resulting N,N-dialkylaniline salt is reacted with thionyl chloride to obtain 5-acetyl-2-alkylbenzenesulfonyl chloride, next the resulting 5-acetyl-2-alkylbenzenesulfonyl chloride is reacted with ammonia to obtain 5-acetyl-2-alkylbenzenesulfonamide then the obtained product is halogenated in a lower alcohol to prepare 2-alkyl-5-haloacetylbenzenesulfonamide.

The above-mentioned reaction steps are shown as follows:

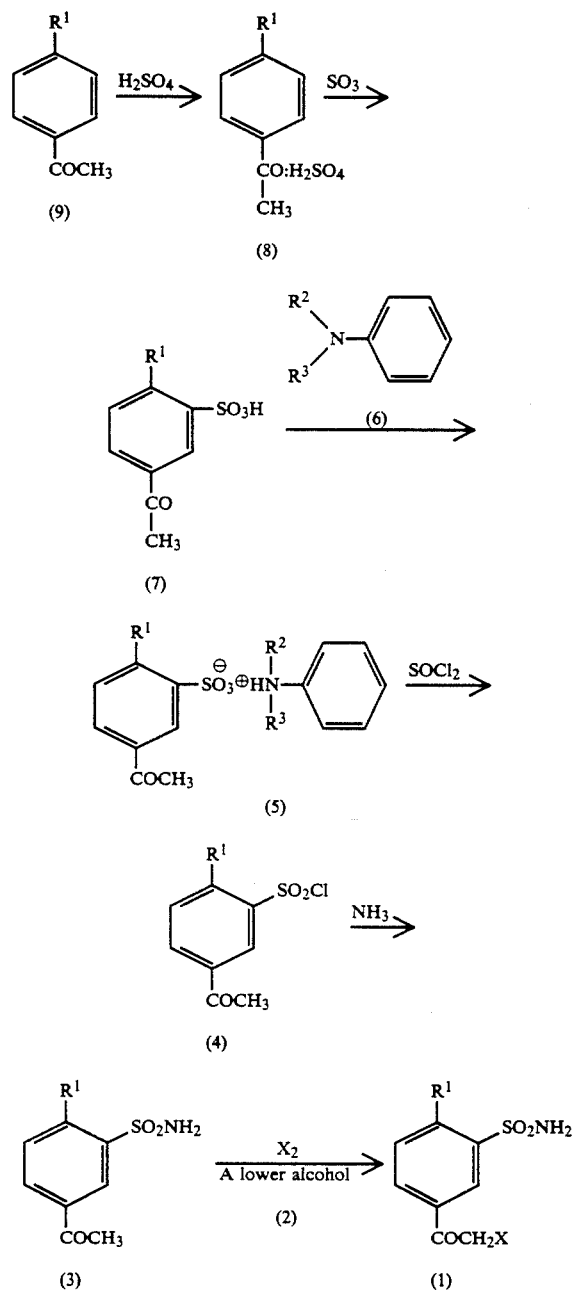

Thus, according to the present invention, 4-alkylacetophenone (9) is coordinated with sulfuric acid to form a sulfuric acid complex (8), then reacted with sulfuric anhydride at a lower temperature to obtain selectively 5-acetyl-2-alkylbenzenesulfonic acid (7), and the resulting product is reacted with N,N-dialkylaniline (6) to prepare N,N-dialkylaniline salt of 5-acetyl-2-alkylbensulfonic acid (5), then reacted with thionyl chloride to prepare 5-acetyl-2-alkylbenzenesulfonyl chloride (4), further reacted with ammonia to obtain 5-acetyl-2-alkylbenzenesulfonamide (3), finally halogenated in a lower alcohol (2) to prepare 2-alkyl-5-haloacetylbenzenesulfonamide (1).

The reaction mechanism of 4-alkylacetophenone with sulfuric acid to form coordinated sulfuric complex (8) has not yet been understood in detail, however, 5-acetyl-2-alkylbenzenesulfonic acid (7) can be obtained selectively in a good yield. Further, the resulting 5-acetyl-2-alkyl-benzenesulfonic acid (7) is changed to its aniline salt (5) and isolated, then this isolated aniline salt (5) is reacted with thionyl chloride to obtain 5-acetyl-2-alkyl-benzenesulfonyl chloride (4) in a high yield. In case that, 4-alkylacetophenone (9) is reacted with sulfuric anhydride or fuming sulfuric acid without using concentrated sulfuric acid, the acetyl group is sulfonated and consequently the desired 5-acetyl-2-methylbenzenesulfonic acid can hardly be obtained.

In the present invention, a concentrated sulfuric acid having about 98% concentration may preferably be used, and 3 to 15 molar quantities, preferably 4 to 8 molar quantities of concentrated sulfuric acid is mixed with 1 molar quantity of 4-alkylacetophenone (9). When concentrated sulfuric acid is used less than 3 molar quantities per molar quantity of 4-alkylacetophenone (9), the yield of the 5-acetyl-2-alkylbenzenesulfonic acid (7) will be lowered. Alternatively, even if 15 molar quantities or more amount of concentrated sulfuric acid is used, the yield of the desired 5-acetyl-2-alkylbenzenesulfonic acid (7) will not be increased and is considered to be uneconomical.

The amount of $SO_3$ in sulfuric anhydride or fuming sulfuric acid to be added after the mixing of concentrated sulfuric acid with 4-alkylacetophenone (9) may suitably be 2 to 15 molar quantities, preferably 4 to 10 molar quantities per molar quantity of 4-alkylacetophenone (9). When less than 2 molar quantities of $SO_3$ is used, the yield of the desired 5-acetyl-2-alkylbenzenesulfonic acid (7) is lowered, alternatively even if 15 molar quantities of more amount of $SO_3$ is used, the yield of the desired 5-acetyl-2-alkylbenzenesulfonic acid (7) will not be increased and is considered to be uneconomical.

The sulfonation may be carried out at lower temperature below 20° C., specifically, a good result can be obtained at a temperature within the range of 0° to 10° C. When the reaction is carried out at a temperature over 20° C., the yield of the desired 5-acetyl-2-alkylbenzenesulfonic acid (7) may be lowered. Alternatively, when the reaction is carried out at a lower temperature below 0° C., it is not advantageous from industrial standpoint.

It is difficult to separate the resulting 5-acetyl-2-alkylbenzenesulfonic acid (7) from the sulfonation mixture in the form of a free acid, so it is preferable to separate it from the reaction mixture as the form of a salt. In view of an economical standpoint, it is separated in the form of sodium 5-acetyl-2-alkylbenzenesulfonate by adding an alkali, especially by adding a required amount of sodium hydroxide. In addition to this, the desired 5-acetyl-2-alkylbenzenesulfonic acid (7) may be separated in the form of an aniline salt (6), which is one of the features of the present invention, in a good yield with economical advantages.

Next, the chlorination of N,N-dialkylaniline salt of 5-acetyl-2-alkylbenzenesulfonic acid (5) may be carried out in the absence of a catalyst. However, in the presence of a catalyst, for example, an organic basic compound such as N,N-dimethylformamide, pyridine, N-methylpyrrolidone, N,N-dimethylacetamide or the like gives a good result. Particularly, a better result can be obtained by using an equimolar mixture of N,N-dimethylformamide with thionyl chloride previously prepared as the chlorinating agent. The chlorination is generally carried out in an organic solvent. As to the organic solvent, any one which does not contain an active hydrogen may be used. For example, tetrahydrofuran, dioxane, diethyl ether, anisol, ethylene glycol dimethyl ether, ethylene glycol diethyl ether, benzene, toluene, xylene, methylene chloride, chloroform, carbon tetrachloride, ethylene dichloride and the like are may be used industrially.

In the chlorination, an equimolar quantity or more, preferably 1.1 to 1.5 molar quantities of thionyl chloride per molar quantity of 5-acetyl-2-alkylbenzenesulfonic acid (7) may be used to give a good result. The chlorination is carried out at a temperature in the range of $-10°$ to 100° C., preferably 0° to 40° C. When the chlorination is carried out at a temperature of too high a condition, the yield of the desired 5-acetyl-2-alkylbenzenesulfonyl chloride (4) may be lowered due to side-reactions and thus no preferable.

In carrying out of the amidation, the 5-acetyl-2-alkylbenzenesulfonyl chloride (4) obtained in the above-mentioned chlorination may be reacted with ammonia without being separated from the reaction mixture of the chlorination. As to the ammonia used in the amidation, generally a common aqueous ammonia may be used, and there is not any restriction in the concentration of the aqueous ammonia. In view of an economical standpoint, 28%-aqueous ammonia may preferably be used. The amidation may preferably be carried out at a lower temperature, and in case of similar to that of the sulfonation, it is preferable to carry out within the range of 0° to 20° C. When the temperature of the amidation exceeds 20° C., the yield of the desired 5-acetyl-2-alkylbenzenesulfonamide (3) may be lower and thus not preferable. Alternatively, when the amidation is carried out below 0° C., it is not advantageous from industrial standpoint.

In carrying out the sulfonation, once 4-alkylacetophenone (9), is coordinated with sulfuric acid, then the resulting coordinated 4-alkylacetophenone compound (8) may be selectively sulfonated at its 3-position, and the resulting 5-acetyl-2-alkylbenzenesulfonic acid (7) is changed to aniline salt thereof (5), further thionyl chloride is used as the chlorinating agent, and ammonia is used as the amidating agent, so that 5-acetyl-2-alkylbenzenesulfonamide (3) can be obtained in a good yield. Thus, the present invention having these features of the above-mentioned reaction steps is an excellent process and it could not have been known in the art.

As to the alkyl group defined in the definitions of $R^1$, $R^2$, and $R^3$, a lower alkyl group having 1 to 5 carbon atoms may be applied generally, and a group having hydrocarbon groups other than the alkyl group, for example, an alkoxy group, aryl group or the like may be widely used.

As to the N,N-dialkylaniline (6) used in the present invention, N,N-dimethylaniline, N,N-diethylaniline, N-ethyl-N-methylaniline, N,N-diisopropylaniline, N,N-di-n-butylaniline and the like may be used, and from reactivity and economical standpoint, N,N-diethylaniline may give the most preferable result.

In carrying out of the sulfonation in an industrial scale, the reaction mixture may be neutralized and then reacted with a protonic acid salt of N,N-dialkylaniline, for example, hydrochloric acid salt of N,N-diethylaniline, so as to separate it in the form of the aniline salt. The amount of N,N-dialkylaniline (6) may be an equimolar quantity or more, generally 1.0 to 1.5 molar quantities. Preferably 1.2 to 1.4 molar quantity per molar quantity of 4-alkylacetophenone may give a good result.

Finally, the resulting 5-acetyl-2-alkylbenzenesulfonamide (3) is halogenated in a lower alcohol (2) so that 2-alkyl-5-haloacetylbenzenesulfonamide (1) can be obtained in a high yield. As to the lower alcohol used in this reaction, there can be exemplified such as methanol, ethanol, n-propanol, n-butanol, isopropyl alcohol, and isobutyl alcohol. From an economical stand point, methanol may preferably be used.

The halogenation is carried out by using chlorine, bromine or iodine, and generally in most cases, the reaction may be carried out by adding bromine to 5-acetyl-2-alkylbenzenesulfonamide (3). The halogenating agent may be selected depending on the type of the desired compound. The amount of the halogenating agent may be an equimolar quantity per molar quantity of 5-acetyl-2-alkylbenzenesulfonamide (3), and may not necessarily be used in an excess amount.

The halogenation reaction may be carried out at a temperature within the range of 20° to 90° C., preferably at a temperature within the range of 30° to 60° C. When the reaction is carried out at too low a temperature, the reaction velocity will be lowered, alternatively, when the reaction is carried out at too high a temperature, side-reactions may be occurred and thus not preferable.

As is explained above, the reaction mechanism of the present invention is not known in detail, and it is considered that the reaction may be proceeded through the following intermediate. Thus, when 5-acetyl-2-alkylbenzenesulfonamide (3) is halogenated in a lower alcohol (2), 2-alkyl-5-haloacetylbenzenesulfonamide diketal (3-a) represented by the following formula may be formed,

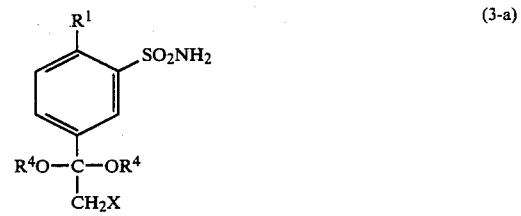

(3-a)

(wherein $R^1$ is the same as defined above; $R^4$ is an alkyl group having 1 to 4 carbon atoms; and X is a chlorine, bromine or iodine atom) then this intermediate (3-a) may be hydrolyzed to form the desired 2-acetyl-5-haloacetylbenzenesulfonamide in a high yield.

The present invention will be illustrated in detail by way of showing the following Examples, but is not restricted only to these Examples.

EXAMPLE 1

Synthesis of N,N-diethylaniline salt of 5-acetyl-2-methylbenzenesulfonic acid 134 Grams (1.0M) of 4-methylacetophenone was added dropwise into 250 g (2.5M) of 98% sulfuric acid by keeping the temperature of the reaction mixture at 15° C., then the reaction mixture was kept at the same temperature and stirred for 30 minutes. Next, by cooling the reaction mixture to 5° C., 861 g of 65% fuming sulfuric acid was added dropwise thereto, the reaction mixture was stirred for 5 hours at the same temperature. The reaction mixture was diluted by pouring it into 2 liters of water, and neutralized with 45% sodium hydroxide aqueous solution. After the neutralization, the temperature of the neutralized solution of the reaction mixture was kept at 40° C., then 462 g of an aqueous solution of N,N-diethylaniline hydrochloride [which contains 222.6 g (1.2M) of N,N-diethylaniline] was added thereto. This mixture was extracted with 890 g of chloroform, and the chloroform layer was concentrated under a reduced pressure, to the residue obtained was added carbon tetrachloride, then the crystals formed were collected by filtration, washed and dried. There were yielded 334 g of white crystals. (Yield=92%, on the basis of 4-methylacetophenone) Melting point: 130°–131° C.

The white crystals were identified as N,N-diethylaniline salt of 5-acetyl-2-methylbenzenesulfonic acid as the results obtained by conducting elementary analysis, IR absorption spectrum and NMR spectrum.

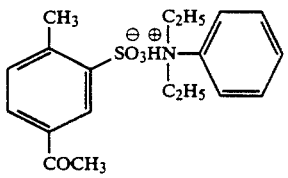

(1) Elementary analysis (for $C_{19}H_{25}NO_4S$ M.W.=363): Calculated (%): C; 62.81, H; 6.89, N; 3.86, S; 8.82. Found (%): C; 62.75, H; 6.91, N; 3.90, S; 8.80.

(2) IR absorption spectrum ($\nu_{max}^{KBr}$ cm$^{-1}$): 3550, 3470, 2610, 2570, 2520, 2460, 1685, 1600, 1485, 1430, 1360, 1260, 1210, 1200, 1100, 1030, 1020, 775, 705, 630, 560.

(3) NMR spectrum ($\delta_{ppm}^{CDCl_3}$, internal standard TMS): 11.2–11.8 (1H, s), 8.6–8.8 (1H, s), 7.8–8.0 (1H, d), 7.3–7.8 (6H, m), 3.5–3.9 (4H, q), 2.8–2.9 (3H, s), 2.5–2.6 (3H, s), 1.0–1.2 (6H, t).

(4) Solubilities: Easily soluble in water, a lower alcohol, chloroform or methylene chloride, and slightly soluble in carbon tetrachloride or hexane.

EXAMPLES 2-3

By a method similar to that described in Example 1, except that sulfuric anhydride was used in place of 65% fuming sulfuric acid, and the following amounts of sulfuric acid as well as sulfuric anhydride were used, there were obtained the results as shown in the following Table 1.

TABLE 1

| Example No. | Amounts (M) 4-Methyl-acetophenone | Sulfuric acid | Sulfuric anhydride | Yield (%) (On the basis of 4-methyl-acetophenone) |
|---|---|---|---|---|
| 2 | 1.0 | 4.1 | 5.0 | 74.9 |
| 3 | 1.0 | 7.3 | 10.1 | 86.8 |

EXAMPLE 4

Synthesis of N,N-dimethylaniline salt of 5-acetyl-2-methylbenzenesulfonic acid By a method similar to that described in Example 1, except that N,N-dimethylaniline was used in place of N,N-diethylaniline, there was obtained N,N-dimethylaniline salt of 5-acetyl-2-methylbenzenesulfonic acid as in the form of an oily substance. Yield: 68.2%.

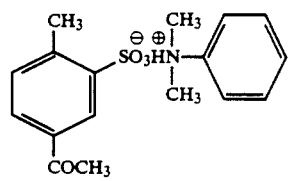

(1) Elementary analysis (for $C_{17}H_{21}NO_4S$, M.W.=335): Calculated (%): C; 60.90, H; 6.27, N; 4.18, S; 9.55. Found (%): C; 60.83, H; 6.31, N; 4.18, S; 9.50.

(2) IR adsorption spectrum ($\nu_{max}^{KBr}$ cm$^{-1}$): 3500, 3050, 2970, 2670, 2620, 2520, 2490, 1690, 1600, 1500, 1470, 1360, 1290, 1250, 1200, 1160, 1130, 1100, 1080, 1020, 770, 700, 630, 560.

(3) NMR spectrum ($\delta_{ppm}^{CDCl_3}$, internal standard TMS) 10.8–11.4 (1H, s), 8.5–8.6 (1H, s), 7.8–8.0 (1H, d), 7.2–7.8 (6H, m), 3.2–3.3 (6H, s), 2.8–2.9 (3H, s), 2.5–2.6 (3H, s).

EXAMPLE 5

Synthesis of N-ethyl-N-methylaniline salt of 5-acetyl-2-methylbenzenesulfonic acid By a method similar to that described in Example 1, except that N-ethyl-N-methylaniline was used in place of N,N-diethylaniline, there was obtained N-ethyl-N-methylaniline salt of 5-acetyl-2-methylbenzensulfonic acid as in the form of an oily substance. Yield: 82%.

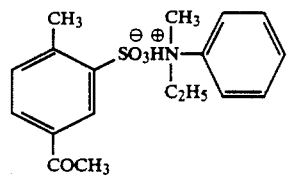

(1) Elementary analysis (for $C_{18}H_{23}NO_4S$, M.W.=349): Calculated (%): C; 61.89, H; 6.59, N; 4.01, S; 9.17. Found (%): C; 61.81, H; 6.64, N; 4.01, S; 9.14.

(2) IR absorption spectrum ($\nu_{max}^{KBr}$ cm$^{-1}$): 3500, 3050, 2610, 2520, 2460, 1690, 1600, 1500, 1485, 1450, 1360, 1250, 1200, 1130, 1100, 1025, 770, 705, 630, 560.

(3) NMR spectrum ($\delta_{ppm}^{CDCl_3}$, internal standard TMS): 10.9–11.5 (1H, s), 8.6–8.7 (1H, s), 7.8–8.0 (1H, s), 7.3–7.8 (6H, m), 3.5–3.9 (2H, q), 3.2–3.3 (3H, s), 2.8–2.9 (3H, s), 2.5–2.6 (3H, s), 1.0–1.2 (3H, t).

EXAMPLE 6

Synthesis of N,N-dibutylaniline salt of 5-acetyl-2-methylbenzenesulfonic acid By a method similar to that described in Example 1, except that N,N-dibutylaniline was used in place of N,N-dimethylaniline, there was obtained N,N-dibutylaniline salt of 5-acetyl-2-methylbenzenesulfonic acid as in the form of an oily substance. Yield: 93.2%.

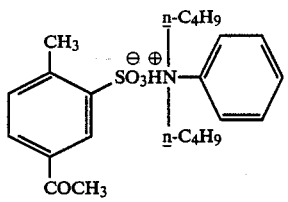

(1) Elementary analysis (for $C_{23}H_{33}NO_4S$, M.W.=419): Calculated (%): C; 65.87, H; 7.88, N; 3.34, S; 7.64. Found (%): C; 65.88, H; 7.93, N; 3.36, S; 7.59.

(2) IR absorption spectrum ($\nu_{max}^{KBr}$ cm$^{-1}$): 3500, 2970, 2890, 2630, 2540, 1690, 1600, 1510 1480, 1360, 1290, 1250, 1170, 1100, 1080, 1020, 750, 700, 730, 580, 560.

(3) NMR spectrum ($\delta_{ppm}^{CDCl_3}$, internal standard TMS): 10.7–11.2 (1H, s), 8.6–8.7 (1H, s), 7.8–8.0 (1H, d), 7.0–7.5 (6H, m), 3.3–3.6 (4H, t), 2.8–2.9 (3H, s), 2.5–2.6 (3H, s), 1.0–1.7 (8H, m), 0.6–0.9 (6H, t).

EXAMPLE 7

Synthesis of 5-acetyl-2-methylbenzenesulfonamide

363 Grams (1.0M) of N,N-diethylaniline salt of 5-acetyl-2-methylbenzenesulfonic acid was dissolved in 934 g of chloroform, to this solution was added a mixture of 80.3 g (1.1M) of N,N-dimethylformamide with 130.9 g (1.1M) of thionyl chloride at a temperature of 2°–3° C., and the whole mixture was stirred at the same temperature for 1 hour. 1,500 Grams of water was added to this reaction mixture, the chloroform layer was separated and washed 3 times with 500 g of water. The chloroform layer was concentrated to obtain 203.1 g (0.874M) of 5-acetyl-2-methylbenzenesulfonyl chloride. The yield was 87.4% on the basis of N,N-diethylaniline salt of 5-acetyl-2-methylbenzenesulfonate.

Thus obtained 5-acetyl-2-methylbenzenesulfonyl chloride was dissolved in 790 g of tetrahydrofuran, then 81 g of ammonia gas was added at a temperature below 10° C. 800 Grams of water was added to this reaction mixture, and tetrahydrofuran was removed by evaporation to crystallized 5-acetyl-2-methylbenzenesulfonamide. The crystals were collected by filtration, and dried to obtain 176.8 g (0.83M) of 5-acetyl-2-methylmethylbenzenesulfonamide. Melting point: 150.5°–151.5° C. The yield was 95% on the basis of 5-acetyl-2-methylbenzenesulfonyl chloride, and was 83% on the basis of N,N-diethylaniline salt of 5-acetyl-2-methylbenzenesulfonate.

EXAMPLES 8–12

By a method similar to that described in Example 7, except that the starting material as shown in the following Table 2 was used respectively in place of N,N-diethylaniline salt of 5-acetyl-2-methylbenzenesulfonate, there were prepared the product as shown in the following Table 2.

TABLE 2

| Example No. | Starting Material | Reaction product | Melting point (°C.) | Yield (%) |
|---|---|---|---|---|
| 8 | N,N-Dimethylaniline salt of 5-acetyl-2-methylbenzenesulfonic acid | 5-Acetyl-2-methylbenzenesulfonamide | 150.5–151.5 | 82.2 |
| 9 | N,N-Di-n-butylaniline salt of 5-acetyl-2-methylbenzenesulfonic acid | 5-Acetyl-2-methylbenzenesulfonamide | 150.5–151.5 | 73.1 |
| 10 | N,N-Diethylaniline salt of | 5-Acetyl-2-n-propylbenzenesulfonamide | 128–129 | 81.3 |

TABLE 2-continued

| Example No. | Starting Material | Reaction product | Melting point (°C.) | Yield (%) |
|---|---|---|---|---|
| | 5-acetyl-2-n-propylbenzenesulfonic acid | | | |
| 11 | N,N-Diethylaniline salt of 5-acetyl-2-ethylbenzenesulfonic acid | 5-Acetyl-2-ethylbenzenesulfonamide | 99–101 | 75.4 |
| 12 | N,N-Diethylaniline salt of 5-acetyl-2-n-butylbenzenesulfonic acid | 5-Acetyl-2-n-butylbenzenesulfonamide | 132–134 | 78.8 |

EXAMPLE 13

Synthesis of 5-bromoacetyl-2-methylbenzenesulfonamide 21.3 Grams (0.1M) of 5-acetyl-2-methylbenzenesulfonamide was dissolved in 180 g of methanol, while the resulting solution was kept at 35°–40° C., 16.0 g (0.1M) of bromine was added dropwise by taking 1.5 hours. The reaction mixture was stirred for 10 minutes after the dropwise addition, 80 g of water was added to the reaction mixture and the whole reaction mixture was stirred for further 30 minutes at room temperature. A part of methanol-water was removed by evaporation, then the crystals formed were collected by filtration, washed with water and dried to obtain 28.0 g of 5-bromoacetyl-2-methylbenzenesulfonamide in the form of white crystals. Melting point: 146.5°–147.5° C. Yield: 95.9%.

EXAMPLES 14–18

By a method similar to that described in Example 13, except that the starting material as shown in the following Table 3 was respectively in place of 5-acetyl-2-methylbenzenesulfonamide, there were prepared the products as shown in the following Table 3.

TABLE 3

| Example No. | Starting Material | Reaction product | Melting point (°C.) | Yield (%) |
|---|---|---|---|---|
| 14 | 5-Acetyl-2-ethyl-benzenesulfonamide | 5-Bromoacetyl-2-ethylbenzenesulfonamide | 92–94 | 94.1 |
| 15 | 5-Acetyl-2-propyl-benzenesulfonamide | 5-Bromoacetyl-2-propylbenzenesulfonamide | 113–114 | 93.1 |
| 16 | 5-Acetyl-2-butyl-benzenesulfonamide | 5-Bromoacetyl-2-butylbenzenesulfonamide | 126–128 | 92.3 |
| 17 | 5-Acetyl-2-methyl-benzenesulfonamide | 5-Chloroacetyl-2-methylbenzenesulfonamide | 162–164 | 90.2 |
| 18 | 5-Acetyl-2-methyl-benzenesulfonamide | 5-Iodoacetyl-2-methylbenzenesulfonamide | 115–117 | 97.2 |

What is claimed is:

1. N,N-Dialkylaniline salt of 5-acetyl-2-alkylbenzene-sulfonic acid represented by the general formula (5),

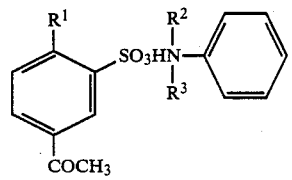

wherein $R^1$ is an alkyl group having 1 to 5 carbon atoms and $R^2$ and $R^3$ are the same or different and are each an alkyl group having 1 to 5 carbon atoms.

2. The N,N-dialkylaniline salt of 5-acetyl-2-alkylbenzenesulfonic acid (5) according to claim 1, wherein $R^1$ is a methyl group; and $R^2$ and $R^3$ are ethyl groups.

* * * * *